United States Patent
Lomoelder et al.

(10) Patent No.: US 9,266,825 B2
(45) Date of Patent: Feb. 23, 2016

(54) COPOLYMERS OF ISOCYANATOALKYLTRIALKOXYSILANES AND URETHANEDIOLS

(71) Applicants: Rainer Lomoelder, Muenster (DE);
Hans Goerlitzer, Dortmund (DE);
Tobias Unkelhaeusser, Herten (DE);
Markus Hallack, Schermbeck (DE);
Wiebke Stache, Recklinghausen (DE)

(72) Inventors: Rainer Lomoelder, Muenster (DE);
Hans Goerlitzer, Dortmund (DE);
Tobias Unkelhaeusser, Herten (DE);
Markus Hallack, Schermbeck (DE);
Wiebke Stache, Recklinghausen (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/616,715

(22) Filed: Feb. 8, 2015

(65) Prior Publication Data
US 2015/0225337 A1    Aug. 13, 2015

(51) Int. Cl.
| | |
|---|---|
| C08G 18/32 | (2006.01) |
| C08G 18/83 | (2006.01) |
| C07C 271/20 | (2006.01) |
| C08G 18/71 | (2006.01) |
| C08G 18/73 | (2006.01) |
| C08G 18/75 | (2006.01) |
| C08G 18/80 | (2006.01) |
| C09D 133/06 | (2006.01) |
| C07C 269/02 | (2006.01) |
| C09D 7/12 | (2006.01) |
| C09D 133/08 | (2006.01) |

(52) U.S. Cl.
CPC ............ *C07C 271/20* (2013.01); *C07C 269/02* (2013.01); *C08G 18/32* (2013.01); *C08G 18/3206* (2013.01); *C08G 18/718* (2013.01); *C08G 18/73* (2013.01); *C08G 18/755* (2013.01); *C08G 18/758* (2013.01); *C08G 18/8016* (2013.01); *C09D 7/125* (2013.01); *C09D 133/06* (2013.01); *C09D 133/08* (2013.01)

(58) Field of Classification Search
None
See application file for complete search history.

(56) References Cited

U.S. PATENT DOCUMENTS

| | | | | |
|---|---|---|---|---|
| 2008/0057316 A1* | 3/2008 | Landon | .................. | C08G 18/10 428/423.1 |
| 2010/0280209 A1* | 11/2010 | Braun | .................... | C08G 18/12 528/28 |

* cited by examiner

*Primary Examiner* — Marc Zimmer
(74) *Attorney, Agent, or Firm* — Oblon, McClelland, Maier & Neustadt, L.L.P.

(57) ABSTRACT

The present invention relates to a copolymer of the formula $$Si(OR)_3-A-N(H)-C(=O)-O-B-O-\left[C(=O)-N(H)-D-N(H)-C(=O)-O-B-O\right]_x-C(=O)-N(H)-A-Si(OR)_3,$$

where A, B, and D are independently of one another an aliphatic (cyclo)alkylene radical, R is a $C_1$-$C_{10}$ alkyl radical, and $3 \leq x \leq 10$. The present invention also relates to a process for preparing the copolymer, to its use and also to a coating composition and a coating formulation containing the copolymer.

15 Claims, No Drawings

COPOLYMERS OF ISOCYANATOALKYLTRIALKOXYSILANES AND URETHANEDIOLS

The present invention relates to copolymers of isocyanatoalkyltrialkoxysilanes and urethanediols, to processes for preparing them, to coating compositions comprising them and to their use.

Modern coatings of all kinds, particularly paint finishes in the automotive sector, are subjected to exacting requirements. Numerous approaches have been undertaken in the past in order to achieve, in particular, high scratch resistances of paints, more particularly of topcoat paints, via combinations of PU crosslinking and silane crosslinking (WO 2008/074489 A1, WO 2008/110229 A2, WO 2006/042658 A1, WO 2008/110230 A1, EP 1 273 640 A2, DE 10 2004 050 747 A1, U.S. Pat. No. 6,428,898 B1). Generally speaking, the scratch resistance is dependent on the crosslinking density, in other words on the amount of silane monomers or $Si(OR)_3$ groups. The relatively high molecular weights of the crosslinkers described in the cited prior art, however, necessitate relatively low solids contents in the coating formulations, leading to deleterious high VOC contents.

Suitability for maximizing levels of —$Si(OR)_3$ groups is possessed by low molecular adducts of linear or branched diols of low molecular mass, and also of polyether polyols and/or polyester polyols, with isocyanatopropyltrialkoxysilanes. Adducts of these kinds are described in WO 2008/034409 A2, WO 2008/131715 A1 and EP 2 641 925 A1, for example. A problem with these systems, however, is the inadequate flexibility of the resulting coatings. A further problem is the high crystallization tendency and low compatibility of adducts of isocyanatopropyltrialkoxysilanes and low molecular mass diols, with the consequence that at the widely desired curing temperatures of below 100° C., there are likely to be flow problems and surface defects in the resultant coating film, as a result of crystallization-induced incompatibilities on the part of the film-forming components. Lastly, the adducts described in the prior art also have the disadvantage that coatings produced with the addition of such adducts do not possess sufficiently good scratch resistance.

It is an object of the present invention, accordingly, to avoid the disadvantages of the known prior art. It is an object of the present invention more particularly to provide copolymers which as an additive in coating formulations, lead to coatings which are particularly scratch-resistant and at the same time are flexible, more particularly in the automotive sector.

This self-imposed object is surprisingly achieved in the present instance by the copolymers of the invention with the generic formula

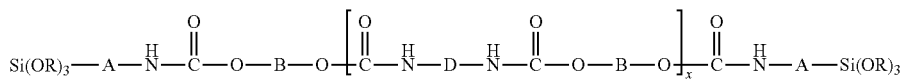

where A, B and D each independently of one another represent (cyclo)alkylene radicals, R represents a $C_1$-$C_{10}$ alkyl radical, and x is between 3 and 10. (Cyclo)alkylene radicals are, equally, cycloalkylene radicals and alkylene radicals. Cycloalkylene radicals, in contrast to the non-cyclic alkylene radicals, are divalent hydrocarbon radicals which consist of or include a non-aromatic hydrocarbon ring system. The radicals A, B and D are preferably alkylene radicals, i.e. divalent, non-cyclic hydrocarbon radicals. A number of radicals A on the copolymer may represent identical or different (cyclo)alkylene radicals. Preferably a number of radicals A in the copolymer, however, represent the same (cyclo)alkylene radical. A number of radicals B on the copolymer may represent identical or different (cyclo)alkylene radicals. Preferably, however, all radicals B in the copolymer represent the same (cyclo)alkylene radical. A number of radicals D on the copolymer may represent identical or different (cyclo)alkylene radicals. Preferably, however, all radicals D in the copolymer represent the same (cyclo)alkylene radical. It is also possible for the radicals R to represent the same $C_1$-$C_{10}$ alkyl radical or to stand for different $C_1$-$C_{10}$ alkyl radicals. $C_1$-$C_{10}$ alkyl radicals, here and below, are alkylene radicals having 1 to 10 carbon atoms. Preferably, however, all radicals R stand for the same $C_1$-$C_{10}$ alkyl radical.

Particularly good properties result if each radical A is selected from the group of linear $C_1$-$C_{10}$ alkylene radicals. $C_1$-$C_{10}$ alkylene radicals, here and below, are alkylene radicals having 1 to 10 carbon atoms. Especially good properties result if each A is a methylene, ethylene, n-propylene or n-butylene radical. Very preferably each A is an n-propylene radical.

Preferably, moreover, each R is selected from the group consisting of methyl, ethyl and isopropyl. More preferably, each R is a methyl radical, since in that case the resulting compounds are particularly reactive.

Corresponding radicals R and A may be introduced into the copolymer of the invention through correspondingly selected isocyanatoalkyltrialkoxysilanes. For instance, corresponding radicals may be introduced through the compounds isocyanatomethyltrimethoxysilane, isocyanatomethyltriethoxysilane, isocyanatomethyltriisopropoxysilane, 2-isocyanatoethyltrimethoxysilane, 2-isocyanatoethyltriethoxysilane, 2-isocyanatoethyltriisopropoxysilane, 3-isocyanato-n-propyltrimethoxysilane, 3-isocyanato-n-propyltriethoxysilane, 3-isocyanato-n-propyltriisopropoxysilane, 4-isocyanato-n-butyltrimethoxysilane, 4-isocyanato-n-butyltriethoxysilane and 4-isocyanato-n-butyltriisopropoxysilane. An especially preferred compound is 3-isocyanato-n-propyltrimethoxysilane.

Particularly good properties result if each radical B is selected from the group of linear, branched or cyclic $C_1$-$C_{12}$ alkylene radicals. Preferred radicals B are n-pentylene, n-hexylene, n-dodecylene, 2,4,4-trimethylhexylene, 2,2,4-trimethylhexylene 2,2,3-trimethylpropylene, 1,1,3-trimethylpropylene, 1,2,3-trimethylpropylene, 2,2-methyl-3-isopropylpropylene, 2-ethyl-3-n-propylpropylene, 2,2-dimethyl-3-n-propylpropylene, 3-methylpentylene, 2-methylpentylene, 2,2-methylpropylene, or cis/trans-1,4-cyclohexylene. Very preferably B is an n-pentylene radical, since the resulting compounds lead to the best results.

Corresponding radicals B may be introduced into the copolymer via the choice of corresponding diols. Preference for this purpose is given to using 1,5-pentanediol, 1,6-hexanediol, 1,12-dodecanediol, 2,2,4-trimethylhexane1,6-diol, 2,4,4-trimethylhexane-1,6-diol, 2,2-dimethylbutane-1,3-diol, 2-methylpentane-2,4-diol, 3-methylpentane-2,4-diol, 2,2,4-trimethylpentane-1,3-diol, 2-ethylhexane-1,3-diol, 2,2-dimethylhexane-1,3-diol, 3-methylpentane-1,5-diol, 2-methylpentane-1,5-diol, 2,2-dimethylpropane-1,3-diol (neopentyl glycol) and cis/trans-1,4-cyclohexanediol (in each case alone or as any desired mixture).

Particularly good properties also result if each radical D is a (cyclo)aliphatic $C_6$-$C_{15}$ alkylene radical. Corresponding radicals may be introduced into the copolymer via the choice of corresponding diisocyanates. Preferred diisocyanates, which lead to particularly advantageous copolymers, are the diisocyanates isophorone diisocyanate (IPDI), hexamethylene diisocyanate (HDI), 4,4'-diisocyanatodicyclohexylmethane (H12MDI), norbornane diisocyanate (NBDI) and also 2,2,4-trimethylhexamethylene diisocyanate and 2,4,4-trimethylhexamethylene diisocyanate (referred to, in the form of a 1:1 mixture, as TMDI). Corresponding radicals D have the structural formulae shown below:

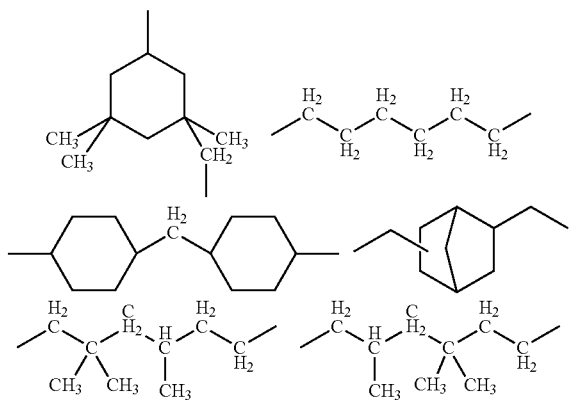

Best results are obtained if the radical D is derived from isophorone diisocyanate, i.e. the structural formula

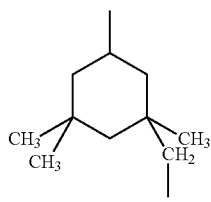

The value for x amounts to a value selected from the values from 3 to 10. The value preferably amounts to a value of 4 to 6. Corresponding values may be brought about by the reaction conditions when the diisocyanate is reacted with the diol. Reducing the solvent fraction, accelerating the addition of diisocyanate, high temperatures, and the initial introduction of the diisocyanate result in higher chain lengths and in an increase in the value x.

The copolymers of the invention may be prepared via a process wherein at least one diol is reacted with at least one diisocyanate to give a urethane intermediate, which is reacted subsequently with at least one isocyanatoalkyltrialkoxysilane.

The reaction of the at least one diol with the at least one diisocyanate takes place in general without solvent or using non-protic solvents. Preferred solvents are ethyl acetate, butyl acetate, ethylene glycol monomethyl ether acetate, ethylene glycol monoethyl ether acetate, 1-methoxyprop-2-yl acetate, 3-methoxy-n-butyl acetate, acetone, 2-butanone, 4-methyl-2-pentanone, cyclohexanone, toluene, xylene, chlorobenzene, white spirit, more highly substituted aromatics (as in commerce, for example, under the designations solvent naphtha, Solvesso®, Isopar® and Nappar® from Deutsche EXXON CHEMICAL GmbH or as Shellsol® from Deutsche Shell Chemie GmbH), carbonic esters (especially dimethyl carbonate, diethyl carbonate, 1,2-ethylene carbonate and 1,2-propylene carbonate), lactones (especially propiolactone, butyrolactone, caprolactone and methylcaprolactone), propylene glycol diacetate, diethylene glycol dimethyl ether, dipropylene glycol dimethyl ether, diethylene glycol ethyl ether acetate, diethylene glycol butyl ether acetate, N-methylpyrrolidone and N-methylcaprolactam. The aforementioned solvents can be used alone or in any desired mixtures. Particular preference is given to using butyl acetate. The reaction is carried out preferably in the absence of water.

The reaction may take place batchwise or continuously. The reaction may be operated at room temperature, in other words at temperatures in the range of 20-25° C., though preferably higher temperatures are used, in the range of 30-150° C., more particularly in the range of 50-150° C. To accelerate the reaction it is possible with advantage to use catalysts which are known within urethane chemistry. Preferred catalysts used are at least one tertiary or aromatic amine (more particularly triethylamine, pyridine, methylpyridine, benzyldimethylamine, N,N-endoethylenepiperazine, N-methylpiperidine, pentamethyldiethylenetriamine, N,N-dimethylaminocyclohexane, N,N'-dimethylpiperazine) and/or at least one metal salt (more particularly iron(II) chloride, aluminium tri(ethylacetoacetate), zinc chloride, zinc(II) n-octanoate, zinc(II) 2-ethyl-1-hexanoate, zinc(II) 2-ethylcaproate, zinc(II) stearate, zinc(II) naphthenate, zinc(II) acetylacetonate, tin (II) n-octanoate, tin(II) 2-ethyl-1-hexanoate, tin(II) ethylcaproate, tin(II) laurate, tin(II) palmitate, dibutyltin(IV) oxide, dibutyltin(IV) dichloride, dibutyltin(IV) diacetate, dibutyltin(IV) dimaleate, dibutyltin(IV) dilaurate, dioctyltin(IV) diacetate, molybdenum glycolate). Where catalysts are used, they are employed preferably in a concentration in the range from 0.001 to 2 wt %, more preferably in the range from 0.005 to 0.5 wt %, based on the total weight of the reactants.

Preferred diols are 1,5-pentanediol, 1,6-hexanediol, 1,12-dodecanediol, 2,2,4-trimethylhexane-1,6-diol and 2,4,4-trimethylhexane-1,6-diol, alone or as any desired mixtures of these isomers, 2,2-dimethyl-butane-1,3-diol, 2-methylpentane-2,4-diol, 3-methylpentane-2,4-diol, 2,2,4-trimethylpentane-1,3-diol, 2-ethylhexane-1,3-diol, 2,2-dimethylhexane-1,3-diol, 3-methylpentane-1,5-diol, 2-methylpentane-1,5-diol, 2,2-dimethylpropane-1,3-diol (neopentyl glycol) and cis/trans-1,4-cyclohexanediol. The diols preferably have a molecular weight of 76 to 314 g/mol, more preferably of 90 to 206 g/mol.

Preferred diisocyanates are isophorone diisocyanate (IPDI), hexamethylene diisocyanate (HDI), 4,4'-diisocyanatodicyclohexylmethane (H12MDI), norbornane diisocyanate (NBDI), and also 2,2,4-trimethylhexamethylene diisocyanate and 2,4,4-trimethylhexamethylene diisocyanate (referred to, as a 1:1 mixture, as TMDI).

The reaction of the at least one diol with the at least one diisocyanate to form the urethane intermediates is accomplished preferably such that the ratio of the OH groups of the diols to the sum of the NCO groups of the diisocyanates is 1:1 to 5:1, more preferably 1.5:1 to 3:1. Very preferably the reaction ratio is 2:1. With more particular preference, therefore, there is complete reaction of all NCO groups of the diisocyanates with OH groups of the diols.

The resulting urethane intermediate is subsequently reacted with at least one isocyanatoalkyltrialkoxysilane. The urethane intermediate here may be used with or without prior isolation. The urethane intermediate is preferably used without prior isolation or purification. Preferred isocyanatoalkyltrialkoxysilanes are isocyanatomethyltrimethoxysilane, isocyanatomethyltriethoxysilane, isocyanatomethyltriisopropoxysilane, 2-isocyanatoethyltrimethoxysilane, 2-isocyanatoethyltriethoxysilane, 2-isocyanatoethyltriisopropoxysilane, 3-isocyanato-n-propyltrimethoxysilane, 3-isocyanato-n-propyltriethoxysilane, 3-isocyanato-n-propyltriisopropoxysilane, 4-isocyanato-n-butyltrimethoxysilane, 4-isocyanato-n-butyltriethoxysilane and 4-isocyanato-n-butyltriisopropoxysilane. Especially preferred is 3-isocyanato-n-propyltrimethoxysilane.

The reaction of the urethane intermediates with the isocyanatoalkyltrialkoxysilanes to form the copolymers of the invention takes place more preferably such that the ratio of OH groups in the urethane intermediates to NCO groups in the isocyanatoalkyltrialkoxysilanes is preferably 0.8:1 to 1.2:1, more preferably 0.9:1 to 1.1:1. Stoichiometric reaction is especially preferred. In particular, therefore, with very particular preference, there is complete reaction of all OH groups of the diols with the NCO groups of the compounds of the isocyanatoalkyltrialkoxysilanes.

In the stated reaction, the NCO groups of the isocyanatoalkyltrialkoxysilanes react with the OH groups of the diols to form —NH—CO—O— groups, which link these compounds to one another.

The reaction of the at least one isocyanatoalkyltrialkoxysilane with the urethane intermediate takes place in general under the same conditions as described above for the reaction of the at least one diol with the at least one diisocyanate.

The copolymers of the invention are liquid in particular at temperatures above 20° C. Depending on the selected stoichiometry of the two reactants, the reaction product may still contain free hydroxyl or isocyanate groups. Preferably, however, the adducts of the invention are substantially free of hydroxyl groups. The adducts of the invention are preferably of medium to high viscosity in solvent-free form, and liquid at 20° C. For greater ease of handling, however, the products may have been admixed with non-protic solvents. The solids contents of such preparations are 50-100%, preferably >80 wt %, and they have a preferred viscosity of 2-80 Pas (DIN EN/ISO 3219 23° C.).

The copolymers of the invention are used advantageously as a crosslinking component for scratch-resistant and flexible clearcoats. In this utility, in order to optimize the coating-material mechanics, they are blended with polymeric binders, which may also carry crosslinkable functional groups. For a curing rate at ambient temperature, however, the reactivity of the copolymers of the invention may not be sufficient. In order to increase the crosslinking rate, therefore, it is possible with preference to add catalysts and/or to carry out the curing at temperatures above ambient temperature.

Suitable for this purpose are chelates, salts or particles of transition metals or other metals, based for example on titanium, aluminium, tin or zirconium complexes, or sulphonic acids, phosphoric acid or phosphorous acids and derivatives thereof, carboxylic acids with melting points of 60° C., quaternary ammonium carboxylates, or else combinations of the compounds stated.

The coating materials for use in the context of the inventive use may be solvent-free or solvent-containing. With more particular preference, the coating materials to be employed are non-aqueous. Non-aqueous in the sense of the present invention means a water content in the coating material of not more than 1.0 wt %, preferably not more than 0.5 wt %, based on the coating material. Particularly in the case of two-component formulations, the aforementioned small amount of water may be used to accelerate the curing. With more particular preference, the coating system employed is free from water (not more than 500 ppm water).

The coating materials obtainable by means of the adducts of the invention may be used in particular for the coating of wood, paper, plastic, glass, textiles or metal. In this way, coatings are obtained which are highly scratch resistant and which crosslink even at temperatures below 100° C.

A further subject of the invention, accordingly, is the use of the copolymers of the invention as coating compositions or as a constituent of coating compositions, more particularly for producing scratch-resistant and flexible clearcoats. Especially preferred are the copolymers which are liquid at temperatures above 0° C.

The coatings obtained on the basis of the above-stated coating compositions are characterized by a high resistance with respect to mechanical stress, and in particular they have a high scratch resistance. Surprising here is that the coatings obtained at the same time have a particularly high flexibility and also a high gloss.

A further subject of the present invention are coating compositions which are curable preferably at temperatures of 20 to 150° C., comprising
  A) at least one copolymer of the invention,
  B) one or more binder components,
  C) optionally up to 4 wt % of at least one catalyst,
  D) optionally auxiliaries and additives,
  E) optionally organic solvents.

The fraction of the copolymers of the invention as component A) in the coating composition of the invention is preferably 30-90 wt %, more preferably 20 to 80 wt %, based on the coating composition.

Furthermore, the coating composition of the invention may optionally comprise one or more binder components B. Suitable in principle as binder components are all kinds of binders known to the skilled person, including, for example, binders which are thermoplastic, in other words not crosslinkable, which customarily have an average molecular weight >10 000 g/mol. Used with preference, however, are binders which possess reactive functional groups having acidic hydrogen atoms. Suitable binders of the stated kind have, for example, at least one, but preferably two or more, hydroxyl group(s). Further suitable functional groups of the binder are trialkoxysilane functionalities, for example.

As binders with functional groups, preference is given to using hydroxyl-containing polymers, more particularly hydroxyl-containing polyesters, polyethers, poly(meth)acrylates, polycarbonates and polyurethanes having an OH number of 20 to 500 mg KOH/g and an average molar mass of 250 to 6000 g/mol. Particular preference in the context of the present invention is given to using hydroxyl-containing polyesters or poly(meth)acrylates having an OH number of 20 to 150 mg KOH/g and an average molecular weight of 500 to 6000 g/mol as binder components. Poly(meth)acrylates here refer both to polyacrylates and to polymethacrylates. The hydroxyl number (OHN) is determined in accordance with DIN 53240-2. In the case of that method, the sample is reacted with acetic anhydride in the presence of 4-dimethylaminopyridine as catalyst, with the hydroxyl groups being acetylated. For each hydroxyl group, this produces one molecule of acetic acid, while the subsequent hydrolysis of the excess acetic anhydride yields two molecules of acetic acid. The consumption of acetic acid is determined by titrimetry from the difference between the main value and a blank value, which is to be carried out in parallel. The molecular weight is determined by means of gel permeation chromatography (GPC). The samples were characterized in tetrahydrofuran as eluent in accordance with DIN 55672-1.

Hydroxyl-containing (meth)acrylic copolymers used may be resins having a monomer composition of the kind described, for example, in WO 93/15849 (page 8, line 25 to page 10, line 5), or else in DE 195 29124. In that case the acid number of the (meth)acrylic copolymer, to be set through proportional use of (meth)acrylic acid as monomer, ought to be 0-30, preferably 3-15 mg KOH/g. The number-average molar weight (determined by gel permeation chromatography against a polystyrene standard) of the (meth)acrylic copolymer is preferably 2000-20 000 g/mol, the glass transition temperature is preferably −40° C. to +60° C. The hydroxyl content of the (meth)acrylic copolymers for use in accordance with the invention, to be set through proportional use of hydroxylalkyl (meth)acrylates, is preferably 70-250 mg KOH/g, more preferably 90-190 mg KOH/g.

Polyester polyols suitable in accordance with the invention are resins having a monomer composition of dicarboxylic and polycarboxylic acids and diols and polyols, of the kind described, for example, in Stoye/Freitag, Lackharze, C. Hanser Verlag, 1996, page 49 or else in WO 93/15849. Polyester polyols used may also be polyadducts of caprolactone with low molecular mass diols and triols, of the kind obtainable under the designation CAPA (Perstorp), for example. The arithmetically determined number-average molar weight is preferably 500-5000 g/mol, more preferably 800-3000 g/mol; the average functionality is preferably 2.0-4.0, more preferably 2.0-3.5.

As urethane- and ester-group-containing polyols for use in accordance with the invention, those employed include in principle those of the kind as described in EP 140 186. Preference is given to using polyols containing urethane and ester groups that are prepared using HDI, IPDI, trimethylhexamethylene diisocyanate (TMDI) or $H_{12}$MDI. The number-average molar weight is preferably 500-2000 g/mol; the average functionality lies more particularly in the range of 2.0-3.5.

Trialkoxysilane-functional binders as well are suitable for use as component B. Such resins may be obtained by copolymerization of acrylate or methacrylate monomers with alkyl-trialkoxysilane derivatives having acrylic or methacrylic functionality (e.g. Dynasylan® MEMO from Evonik Industries AG), of the kind described in WO 92/11328, for example. An alternative synthesis pathway is that of the derivatization of hydroxyl-containing polyethers, polyesters, polycarbonate-diols or polyacrylates with isocyanatopropyl-trialkoxysilane, as is described in Examples 3 and 4 of WO 2008/131715, for example.

Of course, mixtures of the above-described binders may also be used. Preferred binders are hydroxyl-containing polyesters and polyacrylates, alone or in mixtures.

The fraction of B) in the coating composition of the invention is preferably 10-80 wt %, based on the coating composition, more particularly 20 to 80 wt %.

The mass ratio of component A) to component B) in the coating composition of the invention is preferably 3:7 to 7:3.

In order to obtain a sufficient curing rate at curing temperatures of less than 100° C., catalysts C) are preferably employed. Suitable catalysts are, in particular, Lewis acids, chelates, salts or particles of transition or other metals, based for example on titanium, aluminium, tin or zirconium complexes, sulphonic acids in free or else neutralized or adducted form, as are described in DE 2356768, for example, phosphoric acid or phosphorous acids and their derivatives (WO 2008/074491, page 18, lines 1-17), high-boiling acids, quaternary ammonium carboxylates, or else combinations of the stated compounds.

Preference is given to using chelates or salts of transition metals, or high-boiling acids, quaternary ammonium carboxylates, or combinations of the stated compounds.

With particular preference component C) is at least one catalyst selected from the group C1) of the organic carboxylic acids having a melting point above 60° C. and/or from group C2) of the tetraalkylammonium carboxylates.

Suitable organic carboxylic acids having a melting point above 60° C. (under atmospheric pressure) are compounds which are not volatile at room temperature. Examples of carboxylic acids for advantageous use are salicylic acid, benzoic acid, citric acid, isophthalic acid, phthalic acid, terephthalic acid and/or trimellitic acid. Preference in the context of the present invention is given to using salicylic acid and benzoic acid.

Employed as catalyst C2) is a tetraalkylammonium carboxylate. Examples thereof are tetramethylammonium formate, tetramethylammonium acetate, tetramethylammonium propionate, tetramethylammonium butyrate, tetramethylammonium benzoate, tetraethylammonium formate, tetraethylammonium acetate, tetraethylammonium propionate, tetraethylammonium butyrate, tetraethylammonium benzoate, tetrapropylammonium formate, tetrapropylammonium acetate, tetrapropylammonium propionate, tetrapropylammonium butyrate, tetrapropylammonium benzoate, tetrabutylammonium formate, tetrabutylammonium acetate, tetrabutylammonium propionate, tetrabutylammonium butyrate and/or tetrabutylammonium benzoate. The stated tetraalkylammonium carboxylates may be added alone or in mixtures. Preference is given to using tetraethylammonium benzoate and/or tetrabutylammonium benzoate.

The catalyst component C) in the coating compositions of the invention may consist solely of the abovementioned alternatives C1) or C2), although any desired mixtures of the catalysts C1) and C2) may also be used. Such mixtures of C1) and C2) have in particular a ratio of 9:1 to 1:9 (m/m). The fraction of component C) is preferably up to 4 wt %, based on the coating composition, preferably 0.1 to 4 wt %.

The coating composition of the invention may further comprise auxiliaries and/or adjuvants D) known in coating technology, such as stabilizers, including light stabilizers, catalysts, fillers, pigments, flow control agents or rheological assistants, such as sag control agents, for example, microgels or pyrogenic silicon dioxide, in typical concentrations. If necessary, inorganic or organic colour and/or effect pigments customary in coating technology may also be incorporated in component D) of the coating compositions of the invention.

In the case of pigment-free coating compositions, i.e. clearcoat materials, component D) is present preferably in amounts from 0.5 up to 8 wt %, more particularly 1 to 6%, based on the coating composition, in the coating composition of the invention. In the case of pigment- and/or filler-containing coating compositions, the amount of component D) may be 5 to 80 wt %, more particularly 10 to 70 wt %, based on the coating composition.

The coating composition of the invention may further comprise organic solvents as component E). Suitable solvents are, for example, ketones, esters, alcohols or aromatics.

Component E) is present in the coating composition of the invention preferably in amounts from 20 up to 60 wt %, more particularly 20% to 50%, based on the coating composition. The amount of component E) is guided by the target application viscosity for the coating composition.

The sum total of all fractions of components A) to E) makes 100 wt %. The coating compositions of the invention preferably consist of the stated components A) to E).

A further subject of the present invention are coating compositions which are curable preferably at temperatures from 0° to 40° C., comprising I) at least one copolymer of the invention,
II) optionally at least one adduct of at least one isocyanatosilane and at least one hydroxy-functional compound,
III) at least one tin-containing compound and
IV) at least one aminosilane.

The coating composition of the invention may therefore comprise at least one copolymer of the invention, at least one tin-containing compound and at least one aminosilane. It may with further preference comprise at least one copolymer of the invention, at least one adduct of at least one isocyanatosilane and at least one hydroxy-functional compound, at least one tin-containing compound and at least one aminosilane. The coating composition of the invention preferably consists of at least one copolymer of the invention, at least one tin-containing compound and at least one aminosilane or of at least one copolymer of the invention, at least one adduct of at least one isocyanatosilane and at least one hydroxy-functional compound, at least one tin-containing compound and at least one aminosilane. With particular preference the coating composition of the invention consists of a copolymer of the invention, a tin-containing compound and an aminosilane or of a copolymer of the invention, an adduct of at least one isocyanatosilane and at least one hydroxy-functional compound, a tin-compound and an aminosilane.

It has surprisingly emerged that coating compositions made up of these components lead even at 0° C. to stable coatings. These coating compositions of the invention are one-component systems which are easy to apply. They have the advantage, moreover, with a view to subsequent use, of being capable of being formulated and processed without additional organic solvents, by virtue of the low molecular mass fractions of the coating compositions. Hence it is possible in particular to realize a VOC content of below 100 g/l. The amount of components I) and II) in the coating composition of the invention is preferably 10 to 90 wt %, especially preferably 10 to 80 wt %, based in each case on the overall mass of the coating composition.

Component III) of the coating compositions of the invention is a tin-containing compound, preferably an organotin compound. With particular preference it is at least one organic tin compound of the formula $R^1_{4-a}SnX_a$, where a is 1, 2 or 3, $R^1$ is selected independently from the group consisting of linear or branched, optionally substituted $C_1$-$C_{30}$ alkyl groups, $C_5$-$C_{14}$ cycloalkyl groups or $C_6$-$C_{14}$ aryl groups, triorganylsilyl and also $C_1$-$C_{30}$ diorganylalkoxysilyl groups, and X is selected from the group consisting of halogen, —$OR^2$, —$OC(O)R^3$, —OH, —$SR^4$, —$NR^5_2$, —$NHR^6$, —$OSiR^7_3$, —$OSi(OR^8)_3$, in which the substituents $R^2$ to $R^8$ in each case independently of one another are selected from optionally substituted $C_1$-$C_8$ alkyl, $C_6$-$C_{14}$ aryl and/or $C_2$-$C_8$ alkenyl groups.

The linear or branched, optionally substituted $C_1$-$C_{30}$ alkyl groups mentioned in the definition of the aforementioned organic tin compounds include those having 1 to 30 carbon atoms, such as, for example, methyl, ethyl, chloroethyl, n-propyl, isopropyl, n-butyl, isobutyl, pentyl, hexyl, heptyl, ethylhexyl, octyl, decyl, undecyl, dodecyl, tridecyl, etc. Preference is given to butyl, hexyl or octyl.

The $C_5$-$C_{14}$ cycloalkyl groups mentioned in the definition of the above organic tin compounds include mono- or polycyclic alkyl groups, such as, for example, cyclopentyl, cyclohexyl, cyclohexylethyl, cyclooctyl, decalinyl, hydrindanyl, bicyclo[2.2.1]heptanyl, bicyclo[2.2.2]octanyl, bicyclo[4.2.3]nonyl.

$C_6$-$C_{14}$ aryl groups include, for example, phenyl, naphthenyl or fluorenyl groups.

Preferred examples of suitable tin-containing compounds of component III) are alkyltin chlorides and mixtures thereof, as for example di-n-butyltin dichloride and also di-n-octyltin dichloride, or alkyltin oxides and mixtures thereof, as for example di-n-butyltin oxide and di-n-octyltin oxide, dibutyltin carboxylates, as for example di-n-butyltin diacetate, di-n-butyltin dilaurate, di-n-butyltin maleate, di-n-butyltin-bis-2-ethylhexanoate and di-n-butyltin dineodecanoate, dioctyltin carboxylates, such as di-n-octyltin diacetate, di-n-octyltin dilaurate, di-n-octyltin maleate, di-n-octyltin bis-2-ethylhexanoate or di-n-octyltin dineodecanoate, and also dialkyltin complexes, as for example di-n-butyltin diacetylacetonate. Tin compounds which can be used with particular advantage in the mixtures of the invention are generally those which dissolve, immediately or after heating, in the coating compositions of the invention. Especially preferred compounds of component III) are tin ketonates. The amount of the tin-containing compound III) in the coating composition of the invention is preferably 0.01 to 1.0 wt %, especially preferably 0.1 to 1 wt %, based in each case on the coating composition.

Component IV) of the coating compositions of the invention is at least one aminosilane. In particular the at least one aminosilane is one of the general formula $A_m SiY_n$, in which A is a substituted or unsubstituted aminoalkyl group, a substituted or unsubstituted diaminodialkyl group or a substituted or unsubstituted triaminotrialkyl group, the groups Y are identical or different, with Y standing for OH, ONa, OK, OR', OCOR', OSiR'$_3$, Cl, Br, I or NR'$_2$, m is 1 or 2 and n is 1, 2 or 3, with the condition that m+n=4, and the groups R' independently are hydrogen or linear or branched alkyl, cycloalkyl, alkenyl, cycloalkenyl, alkynyl, cycloalkynyl, aryl or heteroaryl groups, have in each case 1 to 18 C atoms, and may in each case optionally be substituted. Preferably m is 1 and n is 3. With further preference Y is selected from OH or OR', with OR' being particularly preferred. In that case R' is selected in particular from methyl or ethyl groups, with methyl groups being especially preferred.

Preferred aminosilanes are those selected from the group consisting of 3-aminopropyltrimethoxysilane, 3-aminopropyltriethoxysilane, 2-aminoethyl-3-aminopropyltrimethoxysilane, 3-aminopropyl(diethoxymethoxysilane), 3-aminopropyl(tripropoxysilane), 3-aminopropyl(dipropoxymethoxysilane), 3-aminopropyl(tridodecanoxysilane), 3-aminopropyl(tritetradecanoxysilane), 3-aminopropyl(trihexadecanoxysilan), 3-aminopropyl(trioctadecanoxysilane), 3-aminopropyl(didodecanoxy)tetradecanoxysilane, 3-aminopropyl(dodecanoxy)-tetradecanoxy(hexadecanoxy)silane, 3-aminopropyl(dimethoxymethylsilane), 3-aminopropyl(methoxydimethylsilane), 3-aminopropyl(hydroxydimethylsilane), 3-aminopropyl(diethoxymethylsilane), 3-aminopropyl(ethoxydimethylsilane), 3-aminopropyl(dipropoxymethylsilane), 3-aminopropyl(propoxydimethylsilane), 3-aminopropyl(diisopropoxymethylsilane), 3-aminopropyl(isopropoxydimethylsilane), 3-aminopropyl(dibutoxymethylsilane), 3-aminopropyl(butoxydimethylsilane), 3-aminopropyl(diisobutoxymethylsilane), 3-aminopropyl(isobutoxydimethylsilane), 3-aminopropyl(didodecanoxymethylsilane), 3-aminopropyl(dodecanoxydimethylsilane), 3-aminopropyl(ditetradecanoxymethylsilane), 3-aminopropyl (tetradecanoxydimethylsilane), 2-aminoethyl (trimethoxysilane), 2-aminoethyl(triethoxysilane), 2-aminoethyl(diethoxymethoxysilane), 2-aminoethyl(tripropoxysilane), 2-aminoethyl(dipropoxymethoxysilane), 2-aminoethyl(tridodecanoxysilane), 2-aminoethyl(tritetradecanoxysilane), 2-aminoethyl(trihexadecanoxysilane), 2-aminoethyl(trioctadecanoxysilane), 2-aminoethyl(didodecanoxy)tetradecanoxysilane, 2-aminoethyl(dodecanoxy)tetradecanoxy(hexadecanoxy)silane, 2-aminoethyl (dimethoxymethylsilane), 2-aminoethyl (methoxydimethylsilane), 2-aminoethyl (diethoxymethylsilane), 2-aminoethyl (ethoxydimethylsilane), 1-aminomethyl(trimethoxysilane), 1-aminomethyl(triethoxysilane), 1-aminomethyl(diethoxymethoxysilane), 1-aminomethyl(dipropoxymethoxysilane), 1-aminomethyl(tripropoxysilane), 1-aminomethyl (trimethoxysilane), 1-aminomethyl (dimethoxymethylsilane), 1-aminomethyl (methoxydimethylsilane), 1-aminomethyl (diethoxymethylsilane), 1-aminomethyl (ethoxydimethylsilane), 3-aminobutyl(trimethoxysilane), 3-aminobutyl(triethoxysilane), 3-aminobutyl(diethoxymethoxysilane), 3-aminobutyl(tripropoxysilane), 3-aminobutyl(dipropoxymethoxysilane), 3-aminobutyl (dimethoxymethylsilane), 3-aminobutyl(diethoxymethylsilane), 3-aminobutyl(dimethylmethoxysilane), 3-aminobutyl (dimethylethoxysilane), 3-aminobutyl (tridodecanoxysilane), 3-aminobutyl (tritetradecanoxysilane), 3-aminobutyl (trihexadecanoxysilane), 3-aminobutyl(didodecanoxy) tetradecanoxysilane, 3-aminobutyl(dodecanoxy) tetradecanoxy(hexadecanoxy)silane, 3-amino-2-methylpropyl(trimethoxysilane), 3-amino-2-methylpropyl (triethoxysilane), 3-amino-2-methyl-propyl (diethoxymethoxysilane), 3-amino-2-methyl-propyl (tripropoxysilane), 3-amino-2-methyl propyl (dipropoxymethoxysilane), 3-amino-2-methyl-propyl (tridodecanoxysilane), 3-amino-2-methyl-propyl (tritetradecanoxysilane), 3-amino-2-methylpropyl (trihexadecanoxysilane), 3-amino-2-methylpropyl (trioctadecanoxysilane), 3-amino-2-methyl-propyl (didodecanoxy)tetradecanoxysilane, 3-amino-2-methyl-propyl(dodecanoxy)tetradecanoxy(hexadecanoxy)silane, 3-amino-2-methyl-propyl(dimethoxymethylsilane), 3-amino-2-methyl-propyl(methoxydimethylsilane), 3-mercapto-2-methyl-propyl(diethoxymethylsilane), 3-mercapto-2-methyl-propyl(ethoxydimethylsilane), 3-mercapto-2-methyl-propyl(dipropoxymethylsilane), 3-amino-2-methyl-propyl(propoxydimethylsilane), 3-amino-2-methyl-propyl (diisopropoxymethylsilane), 3-amino-2-methyl-propyl (isopropoxydimethylsilane), 3-amino-2-methyl-propyl (dibutoxymethylsilane), 3-amino-2-methyl-propyl (butoxydimethylsilane), 3-amino-2-methyl-propyl (diisobutoxymethylsilane), 3-amino-2-methyl-propyl (isobutoxydimethylsilane), 3-amino-2-methyl-propyl (didodecanoxymethylsilane), 3-amino-2-methyl-propyl (dodecanoxy-dimethylsilane), 3-amino-2-methyl-propyl (ditetradecanoxymethylsilane) or 3-amino-2-methylpropyl (tetradecanoxydimethylsilane), triamino-funtional propyltrimethoxysilane, bis(3-trimethoxysilylpropyl)amine, bis(3-triethoxysilylpropyl)amine, N-benzyl-N-(2-aminoethyl)-3-aminopropyltrimethoxysilane hydrochloride, N-benzyl-N-(2-aminoethyl)-3-aminopropyltrimethoxysilane hydroacetate, N-(n-butyl)-3-aminopropyltrimethoxysilane, 3-aminopropylmethyldiethoxysilane, N-vinylbenzyl-N-(2-aminoethyl)-3-aminopropylpolysiloxane and N-(2-aminoethyl)-3-aminopropylmethyldimethoxysilane.

Preferred aminosilanes or aminoalkylsilanes are substituted or unsubstituted aminosilane compounds, especially 3-aminopropyltrimethoxysilane, 3-aminopropyltriethoxysilane, 3-aminopropylmethyldiethoxysilane, N-(2-aminoethyl)-3-aminopropyltrimethoxysilane, 2-aminopropyl-3-aminopropyltrimethoxysilane, 2-aminopropyl-3-aminopropyltriethoxysilane, 2-aminoethyl-2-aminoethyl-3-aminopropyltrimethoxysilane, 2-aminoethyl-2-aminoethyl-3-aminopropyltriethoxysilane and N-(n-butyl)-3-aminopropyltrimethoxysilane.

With particular preference the aminosilane is one selected from the group consisting of 3-aminopropyltrimethoxysilane (DYNASYLAN® AMMO), 3-aminopropyltriethoxysilane (DYNASYLAN® AMEO), 3-aminopropylmethyldiethoxysilane (DYNASYLAN® 1505), N-(n-Butyl)-3-aminopropyltrimethoxysilane (DYNASYLAN® 1189) and N-(2-aminoethyl)-3-aminopropyltrimethoxysilane (DYNASYLAN® DAMO), $(H_3CO)_3Si(CH_2)_3NH(CH_2)_3Si(OCH_3)_3$ (bis-AMMO), $(H_5C_2O)_3Si(CH_2)_3NH(CH_2)_3Si(OC_2H_5)_3$ (bis-AMEO), $(H_3CO)_3Si(CH_2)_3NH(CH_2)_2NH(CH_2)_2NH(CH_2)_3Si(OCH_3)_3$ (bis-DAMO) (in each case from Evonik Industries AG).

The amount of component IV) of the coating composition of the invention is preferably 5 to 30 wt %, especially preferably 10 to 20 wt %, based in each case on the coating composition. The coating compositions of the invention are produced by mixing of the components described above. The mixing may be accomplished in mixers known to the skilled person, examples being stirring vessels, dissolvers, bead mills, roll mills, etc., or else continuously by means of static mixers.

The present invention likewise provides metal-coating formulations, especially for car bodies, cycles and motorcycles, building components and household appliances, comprising the copolymers or coating compositions of the invention.

Coating formulations for glass, plastic, paper, textile or wood coatings, more particularly clearcoat materials, comprising the adducts or coating compositions of the invention are likewise provided by the present invention. The coating compositions of the invention are also suitable for multi-coat finishing, for example as clearcoat material in automotive OEM finishing.

Even without further observations, it is assumed that a skilled person is able to utilize the above description to its widest extent. The preferred embodiments and examples are therefore to be interpreted merely as a descriptive disclosure which is by no means limiting in any way whatsoever. The present invention is elucidated in more detail below using examples. Alternative embodiments of the present invention are obtainable analogously.

EXAMPLES

Unless otherwise indicated, the quantity figures in percent in the examples are given by weight.

Example a

Preparation of Inventive Copolymer 1

A three-necked flask with reflux condenser and dropping funnel is charged with 21.09 g of 1,5-pentanediol, 0.01 g of DBTL (dibutyltin(IV) dilaurate) and 10 g of butyl acetate, and this initial charge is heated to 60° C. under a nitrogen atmosphere. The mixture, initially turbid, becomes clear at about 55° C. At 60° C., over the course of 1.5 hours, 26.58 g of H12MDI are added dropwise, the reaction mixture being turbid. The end of metering is followed by 30 minutes of stirring at 60° C., after which the NCO content is measured. When the NCO content is <0.1%, 42.23 g of isocyanatopropyltrimethoxysilane (IPMS) are added dropwise at not more than 60° C. After 2.5 hours of addition, the addition of IPMS is at an end, and is followed by 1-2 hours of stirring at 60° C. The resulting copolymer 1 is a liquid which is turbid at room temperature and has a viscosity (23° C.) of 21 Pas (see also Table 1.

Examples b-e

Preparation of Inventive Copolymers 2-5

As for Example a, the amounts of the diol, the catalyst and the butyl acetate solvent indicated in Table 1 are introduced and heated to 60° C. The stated amount of diisocyanate is added dropwise to the clear solution at 60° C. over the course of 1.5 hours. After a reaction time of 0.5-1 hour at 60° C., an NCO content of <0.1% is reached. Subsequently the stated amount of isocyanatopropyltrimethoxysilane (IPMS) is added dropwise at not more than 60° C. After 2.5 hours of addition, the addition of IPMS is at an end, and is followed by 1-2 hours of stirring at 60° C. The properties of the resulting copolymers 2-5 are likewise reported in Table 1.

f1b: Preparation of Polyester Precursor 7a 587 g of pentanediol, 412 g of adipic acid and 1 g of Tegokat 256 were introduced, and the esterification reaction was carried out as for f1a. After a reaction time of 6.5 hours, the reaction mixture was obtained with a hydroxyl number of 112 mg KOH/g. It was admixed with 329.3 g of pentanediol. Following homogenization, polyester precursor 7a was obtained with a hydroxyl number of 373 mg KOH/g.

f2a: Preparation of Non-Inventive Copolymer 6

The 246.2 g of polyester precursor 6a and 0.17 g of DBTL were charged to a glass flask with reflux condenser and dropping funnel, and this initial charge was heated to 50° C. with stirring. Subsequently, over the course of 3 hours, at not more than 70° C., 314.4 g of isocyanatopropyltrimethoxysilane (IPMS) were added dropwise. After a reaction time of 3 hours at 70° C., copolymer 6 was obtained with an NCO content >0.1%.

f2b: Preparation of Non-Inventive Copolymer 7

The 243.6 g of polyester precursor 7a and 0.17 g of DBTL were charged to a glass flask with reflux condenser and dropping funnel, and this initial charge was heated to 50° C. with stirring.

Subsequently, over the course of 3 hours, at not more than 70° C., 333.2 g of isocyanatopropyltrimethoxysilane (IPMS)

TABLE 1

Overview of the preparation of inventive copolymers 1-5

| | Example | | | | |
|---|---|---|---|---|---|
| | a | b | c | d | e |
| | Copolymer | | | | |
| | 1 | 2 | 3 | 4 | 5 |
| Pentanediol | 21.5% | 22.19% | 22.39% | | |
| Hexanediol | | | | 24.4% | |
| Neopentyl glycol | | | | | 22.08% |
| H12MDI | 26.58% | | | | |
| IPDI | | 23.72% | | 22.87% | 23.62 |
| TMDI | | | 22.66% | | |
| Butyl acetate | 10 | 10 | 10 | 10 | 10 |
| IPMS | 42.32% | 44.07% | 44.93% | 42.89% | 44.30% |
| Reaction time | 6 h | 5 h | 7 h | 5 h | 6 h |
| Properties | | | | | |
| NCO content | <0.1% | <0.1% | <0.1% | <0.1% | <0.1% |
| Viscosity (23° C.) | 21 Pas | 14 Pas | 2.8 Pas | 12 Pas | 79 Pas |
| Appearance | Turbid | Clear | Turbid | Clear | Clear |

Example f

Preparation of Non-Inventive Copolymers 6-7

F1a: Preparation of Polyester Precursor 6a

A stirred vessel with distillation bridge was charged with 284 g of pentanediol, 431 g of adipic acid, 284 g of trimethylolpropane and 1 g of Tegokat 256. With stirring, the reaction mixture was heated and at 145-201° C./1013-1065 mbar pressure, the water produced during the esterification was distilled off. After a reaction time of 8.5 hours, polyester precursor 6a was obtained with a hydroxyl number of 348 mg KOH/g.

were added dropwise. After a reaction time of 3 hours at 70° C., copolymer 7 was obtained with an NCO content >0.1%.

Example g

Preparation of Non-Inventive Copolymer 8

In a three-necked flask with reflux condenser and dropping funnel, 28.7 g of isocyanatopropyltrimethoxysilane (IPMS), 71.3 g of Oxyester T1136 and 0.1% of DBTL are weighed out, blanketed with nitrogen and heated to 60° C. with stirring. After a reaction time of about 15 hours at 60° C., an NCO content of <0.1% is reached. The resulting copolymer 8 is a liquid which is clear at room temperature and has a viscosity (23° C.) of 4 Pas (see also Table 1).

Example h

Investigation of the Materials Properties of Various Inventive Clearcoat Materials in Comparison to Conventional 2-Component PU Clearcoat Materials and to Non-Inventive Clearcoat Materials Comprising Adducts of Diols and/or Polyesters and isocyanatopropyltrialkoxysilanes The inventive clearcoat materials (formulations: II, V, VI, VIII, IX, X) and also the comparison based on two 2-component PU clearcoat materials (formulations: I, IV) and non-inventive clearcoat materials comprising adducts of diols and/or polyesters and isocyanatopropyltrialkoxysilanes (formulations: III, VII, XI, XII) were formulated in accordance with the quantity parts indicated in Table 2.

The viscosity of the formulations, determined as the flow time in the DIN 4 cup at 23° C., was approximately 20 seconds.

The mechanical characteristics were determined by applying all of the coating materials by spraying with compressed air assistance, using an HPLV gun, to phosphatized steel panels (Chemetall Gardobond 26S160100) and curing them under different baking conditions (room temperature, 30' 80° C., 22' 140° C.).

Testing for scratch resistance took place in a two-coat system, the clearcoat over a black basecoat. For this purpose, an aqueous black basecoat material (Autowave MM 245, jet black; blended 100:5 with Aktivator WB, curing: 15' 50° C.) was applied by spraying to—in the case of acid resistance—metal test panels of special deep-drawn material with RP surface to DIN 1624, 570×98×0.8 mm, and—in the case of

TABLE 2

Constitution of the inventive clearcoat materials and comparative examples

| Item | | I | II | III | IV | V | VI | VII | VIII | IX | X | XI | XII |
|---|---|---|---|---|---|---|---|---|---|---|---|---|---|
| 1 | Copolymer 1 | / | / | / | / | / | / | / | / | / | 89.9 | / | / |
| 2 | Copolymer 2 | / | 39.58 | / | / | / | / | / | 26.73 | / | / | / | / |
| 3 | Copolymer 3 | / | / | / | / | / | / | / | / | 28.02 | / | / | / |
| 4 | Copolymer 4 | / | / | / | / | / | 24.78 | / | / | / | / | / | / |
| 5 | Copolymer 5 | / | / | / | 24.78 | / | / | / | / | / | / | / | / |
| 6 | Copolymer 6 | / | / | / | / | / | / | 25.38 | / | / | / | / | / |
| 7 | Copolymer 7 | / | / | 26.93 | / | / | / | / | / | / | / | / | / |
| 8 | Copolymer 8 | / | / | / | / | / | / | / | / | / | / | 25.0 | / |
| 9 | Dynasylan AMMO | / | / | / | / | / | / | / | / | / | 10 | 10 | 10 |
| 10 | VESTANAT EP-M 95 | / | / | / | / | / | / | / | / | / | / | 64.9 | 89.9 |
| 11 | Setalux ® 1767 VV-65 (65% form) | 52.20 | / | / | / | / | / | / | / | / | / | / | / |
| 12 | Setalux ® 1760 VB-64 (64% form) | / | 23.86 | 42.08 | 49.47 | 34.85 | 34.85 | 39.65 | 37.60 | 39.40 | / | / | / |
| 13 | VESTANAT ® HT 2500 L (90% form) | 19.24 | / | / | 14.51 | / | / | / | / | / | / | / | / |
| 14 | TEAB | / | 0.51 | 0.54 | / | 0.45 | 0.45 | 0.76 | 0.96 | 1.01 | / | / | / |
| 15 | DBTL | / | / | / | / | / | / | / | / | / | 0.1 | 0.1 | 0.1 |
| 16 | Byketol ® special | 2.60 | / | / | / | / | / | / | / | / | / | / | / |
| 17 | Byk ® 301 | 0.20 | / | / | / | / | / | / | / | / | / | / | / |
| 18 | Tego ® Glide 410 | / | 0.05 | 0.05 | 0.05 | 0.05 | 0.05 | 0.05 | 0.05 | 0.05 | / | / | / |
| 19 | Tinuvin ® 292 | 0.26 | 0.25 | 0.27 | 0.22 | 0.22 | 0.22 | 0.25 | 0.24 | 0.24 | / | / | / |
| 20 | Tinuvin ® 900 | 3.26 | 3.19 | 3.37 | 2.80 | 2.76 | 2.76 | 3.17 | 2.98 | 3.04 | / | / | / |
| 21 | Butyl acetate/xylene mixture (1:1) | 22.24 | 32.56 | 26.76 | 32.95 | 36.89 | 36.89 | 30.74 | 31.44 | 28.24 | | | |

Setalux ® 1767 VV-65: Polyacrylate polyol, Nuplex Resins B.V.
Setalux ® 1760 VB-64: Polyacrylate polyol, Nuplex Resins B.V.
Byk ® 301: Polyether-modified polydimethylpolysiloxane, flow control agent, Byk Chemie
Byketol ® Special: Flow control agent based on high-boiling solvents and polyether-modified polydimethylsiloxanes, Byk Chemie
Tinuvin ® 292: Sterically hindered amine, light stabilizer; BASF SE
Tinuvin ® 900: UV absorber; BASF SE All of the 2-component PU clearcoat materials (formulations I, IV) were formulated as 2-components systems, meaning that the curing component (item 13) and the polyol components (items 11-12) were mixed immediately prior to processing. In the case of the inventive clearcoat materials (formulations II, V, VI, VIII, IX) the same procedure was adopted. Inventive copolymers 2-5 were mixed with the polyol component (item 12) immediately prior to processing. In the case of the inventive clearcoats (formulation X), the inventive copolymer 1 was combined with an aminosilane (item 9) in one-component form. A similar one-component combination with an adduct, composed of diols and IPMS (item 10) and an aminosilane (item 9), was realized for formulations XI and XII.

scratch resistance—to metal bodywork panels (steel, 190×105×0.8 mm DIN 1624) and, after a flash-off time of 10 minutes at room temperature, were dried in a forced air oven at 80° C. for 10 minutes. The dry film thickness in each case is about 10 μm.

For the test for scratch resistance, a nylon fabric 45 mm×20 mm with a mesh size of 25 μm, is weighted with a 2 kg weight, and placed on and locked to the test plate, which is in turn fixed on a carriage. Following application of 1 ml of an agitated, 0.25% strength detergent solution (Persil) immediately in front of the test area, the test plate is oscillated with a maximum deflection in each case of about 3.5 cm. After 80 double rubs (1 s$^{-1}$), the remaining wash fluid is rinsed off with mains water and dried with compressed air. Gloss measurements (20° angle) are performed before and after the test in each case.

TABLE 3

Properties of clearcoats I to III

| | Composition | | |
|---|---|---|---|
| | I | II | III |
| Curing | 22' 140° C. | 22' 140° C. | 22' 140° C. |
| Pendulum hardness (König) [s] n 7 d | 171 | 184 | 70 |
| Ball impact [in lbs] (DIN-EN-ISO 6272-1) | 80 | >80 | >80 |
| MEK test [ASTM D 4752] (Double rubs, 1 kg applied weight) | >150 | >150 | >150 |
| Scratch resistance Initial gloss/loss of gloss [scale divisions] | 79/20 | 83/7 | 84/0 |

The results in Table 3 demonstrate that the inventive clearcoat (formulation II) exhibits outstanding scratch resistance and is far superior in this respect to the 2-component PU coating (formulation I). Formulation III, comprising an adduct of a polyester and isocyanatopropyltrialkoxysilane (copolymer 7), is substantially softer by comparison with, and in this respect significantly inferior to, the inventive coating composition.

TABLE 4

Properties of clearcoats IV to VII

| | Composition | | | |
|---|---|---|---|---|
| | IV | V | VI | VII |
| Curing | 30' 80° C. | 30' 80° C. | 30' 80° C. | 30' 80° C. |
| Pendulum hardness (König) [s] n 7 d | 188 | 195 | 186 | 72 |
| Ball impact [in lbs] (DIN-EN-ISO 6272-1) | >80 | 60 | 80 | 80 |
| MEK test [ASTM D 4752] (Double rubs, 1 kg applied weight) | >150 | >150 | >150 | >150 |
| Scratch resistance Initial gloss/loss of gloss [scale divisions] | 87/44 | 87/21 | 88/14 | / |

The results in Table 4 demonstrate that the inventive clearcoats (formulation V, VI) exhibit outstanding scratch resistance and in that respect are far superior to the 2-component PU coating (formulation IV). Formulation VII, comprising an adduct of a polyester and isocyanatopropyltrialkoxysilane (copolymer 6), is substantially softer by comparison with, and in this respect significantly inferior to, the inventive clearcoats.

TABLE 5

Properties of clearcoats IV, VIII and IX

| | Composition | | |
|---|---|---|---|
| | IV | VIII | IX |
| Curing | RT | RT | RT |
| Pendulum hardness (König) [s] n 7 d | 127 | 120 | 154 |

TABLE 5-continued

Properties of clearcoats IV, VIII and IX

| | Composition | | |
|---|---|---|---|
| | IV | VIII | IX |
| Ball impact [in lbs] (DIN-EN-ISO 6272-1) | >80 | 80 | 50 |
| MEK test [ASTM D 4752] (Double rubs, 1 kg applied weight) | 135 | >150 | >150 |
| Scratch resistance Initial gloss/loss of gloss [scale divisions] | 90/40 | 85/17 | 90/32 |

The results in Table 5 demonstrate that the inventive clearcoats (formulations VIII, IX) have a scratch resistance superior to the 2-component PU coating (formulation IV) and are at the same level in terms of hardness, flexibility and chemical resistance.

TABLE 6

Properties of clearcoats X to XII

| | Composition | | |
|---|---|---|---|
| | X | XI | XII |
| Curing | RT | RT | RT |
| Pendulum hardness (König) [s] n 7 d | 120 | 108 | 134 |
| Erichsen cupping [mm] (EN ISO 1520) | 5 | 2.5 | 1.5 |
| MEK test [ASTM D 4752] (Double rubs, 1 kg applied weight) | >150 | >150 | >150 |

The results in Table 6 demonstrate that the inventive clearcoat (formulation X), which like formulations XI and XII represents a one-component system, exhibits the most balanced profile of properties by comparison with those formulations. Here as well it is possible to achieve not only a comparatively high hardness but at the same time a high flexibility for the coating, which is lost if inventive copolymer 1 is not used.

The invention claimed is:

1. A copolymer of formula

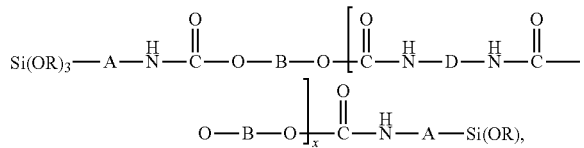

where
A, B, D are independently an aliphatic (cyclo)alkylene radical,
R is a $C_1$-$C_{10}$ alkyl radical, and
$3 \leq x \leq 10$.

2. The copolymer according to claim 1, wherein each A is independently a linear $C_1$-$C_{10}$ alkylene radical.

3. The copolymer according to claim 1, wherein each R is independently a methyl, ethyl or isopropyl radical.

4. The copolymer according to claim 1, wherein each B is independently a linear, branched or cyclic $C_1$-$C_{12}$ alkylene radical.

5. The copolymer according to claim 1, wherein each D is independently a (cyclo)aliphatic $C_6$-$C_{15}$ alkylene radical.

6. The copolymer according to claim 5, wherein each D independently has a structural formula selected from the group consisting of

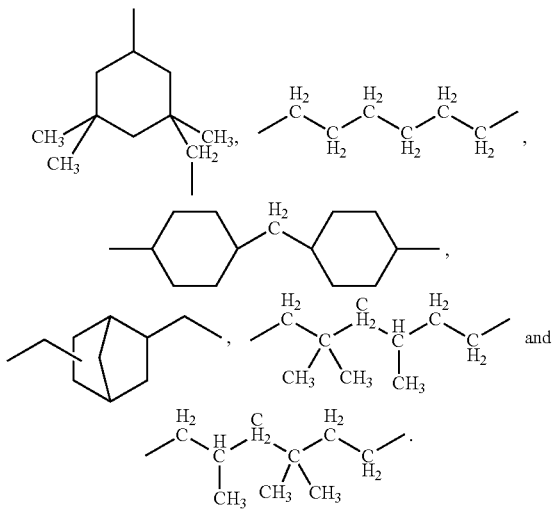

7. A process for preparing the copolymer according to claim 1, the process comprising:
reacting at least one diol with at least one diisocyanate to give a urethane intermediate, and
subsequently reacting the urethane intermediate with at least one isocyanatoalkyltrialkoxysilane.

8. A coating composition or a constituent of a coating composition, comprising:
the copolymer according to claim 1.

9. A coating composition, comprising:
A) at least one copolymer according to claim 1,
B) a binder component,
C) optionally up to 4 wt % of a catalyst,
D) optionally an auxiliary and an additive, and
E) optionally an organic solvent.

10. The coating composition according to claim 9, wherein component B) is selected from the group consisting of a hydroxyl-comprising polyester, a polyether, a poly(meth) acrylate, a polycarbonate and a polyurethane having an OH number of from 20 to 500 mg KOH/g and an average molar mass of from 250 to 6000 g/mol.

11. The coating composition according to claim 9, wherein component C) is at least one catalyst selected from the group consisting of: C1) an organic carboxylic acid having a melting point above 60° C. and C2) a tetraalkylammonium carboxylate.

12. The coating composition according to claim 11, wherein component C2) is at least one selected from the group consisting of tetramethylammonium formate, tetramethylammonium acetate, tetramethylammonium propionate, tetramethylammonium butyrate, tetramethylammonium benzoate, tetraethylammonium formate, tetraethylammonium acetate, tetraethylammonium propionate, tetraethylammonium butyrate, tetraethylammonium benzoate, tetrapropylammonium formate, tetrapropylammonium acetate, tetrapropylammonium propionate, tetrapropylammonium butyrate, tetrapropylammonium benzoate, tetrabutylammonium formate, tetrabutylammonium acetate, tetrabutylammonium propionate, tetrabutylammonium butyrate and tetrabutylammonium benzoate.

13. A coating composition, comprising:
I) at least one copolymer according to claim 1,
II) optionally an adduct of at least one Isocyanatosilane and at least one hydroxy-functional compound,
III) a tin-comprising compound and
IV) an aminosilane.

14. A coating formulation for metal, glass, plastic, paper, textile or wood, the coating formulation comprising:
at least one copolymer according to claim 1.

15. A coating formulation for metal, glass, plastic, paper, textile or wood, the coating formulation comprising:
at least one coating composition according to claim 9.

* * * * *